United States Patent [19]

Bellus

[11] 4,159,387

[45] Jun. 26, 1979

[54] SQUARIC ACID ESTERS

[75] Inventor: Daniel Bellus, Riehen, Switzerland

[73] Assignee: Ciba-Geigy Corporation, Ardsley, N.Y.

[21] Appl. No.: 854,287

[22] Filed: Nov. 23, 1977

[30] Foreign Application Priority Data

Dec. 3, 1976 [CH] Switzerland ............... 15254/76

[51] Int. Cl.$^2$ ............... C07C 43/14; C07C 43/18; C07C 49/45; C07C 69/145
[52] U.S. Cl. ............................. 560/185; 560/187; 560/188; 560/228; 560/231; 260/586 R; 568/598
[58] Field of Search ............... 560/185, 187, 188, 228, 560/231; 260/611 R, 586 R

[56] References Cited

U.S. PATENT DOCUMENTS

| | | | |
|---|---|---|---|
| 3,059,030 | 10/1962 | Park et al. ................. | 260/611 R |
| 3,288,854 | 11/1966 | Martin ....................... | 260/611 R |
| 3,819,677 | 6/1974 | Gale .......................... | 260/611 R |
| 4,092,146 | 5/1978 | Fischer et al. ............. | 71/70 |

OTHER PUBLICATIONS

Ooms, Pieter J. J. et al., "Chemistry of Tetra-alkoxyethenes," Pts. VI & VII, J. Chem. Soc. (London), Perkin I (1976), pp. 1533–1538 & 1538–1543.

*Primary Examiner*—Bernard Helfin
*Assistant Examiner*—L. Hendriksen
*Attorney, Agent, or Firm*—Luther A. R. Hall

[57] ABSTRACT

There are described new squaric acid esters, particularly mono-ortho esters, di-ortho esters, ortho ester anhydrides and ortho ester halides of squaric acid; a new process for producing these squaric acid esters; and a process for converting the squaric acid esters into squaric acid. It is possible by the new process to produce, with the use of readily obtainable starting products, the new squaric acid esters according to the invention in an economical manner and with good to very good yields; and the squaric acid esters can be converted under mild reaction conditions into squaric acid.

13 Claims, No Drawings

SQUARIC ACID ESTERS

The present invention relates to new squaric acid esters, particularly to mono-ortho esters, diortho esters, ortho ester anhydrides and ortho ester halides of squaric acid; to a new process for obtaining them; and to their use for producing squaric acid (diketocyclobutenediol).

Various processes for producing squaric acid are known from the literature. A process known from 'Angew. Chemie, 75, 982 (1963)' comprises firstly reacting hexachlorobutadiene with ethylate to 1-ethoxypentachlorobutadiene-1,3. This can be then cyclised thermocatalytically at about 200° C. to perchlorocyclobutenone, from which squaric acid can be obtained by hydrolysis at temperatures between 100° and 110° C., preferably in the presence of concentrated sulphuric acid.

According to a further process, squaric acid can be produced by reacting hexachlorobutadiene with excess morpholine; adjusting the pH value of the reaction mixture to 5–9 with dilute aqueous acid, e.g. with dilute hydrochloric acid; stirring at a temperature of 20°–100° C.; then strongly acidifying the resulting mixture and heating it to boiling. There is formed as intermediate trichlorotrimorpholino-butadiene, which converts in an aqueous medium at pH 5–9 to $\beta$-morpholino-trichlorocyclobutenone. From this is formed, by acid hydrolysis, squaric acid in about 40% yield, relative to the hexachlorobutadiene (German Offenlegungsschrift No. 1,568,291).

It is known from U.S. Pat. No. 3,059,030 and from J. Am. Chem. Soc. 84, 2919 (1962) and 85, 2584 (1963) that fluorinated cyclobutenes or cyclobutanes, such as 1,2-dialkoxy-3,3,4,4-tetrafluorocyclobutene, 1,3,3-trialkoxy-2-chloro-4,4-difluorocyclobutene or 1,1,3,3-tetramethoxy-2-chloro-4,4-difluorocyclobutane, can be converted into squaric acid by hydrolysis at a temperature of at least 100° C. The hydrolysis has to be partially performed in an autoclave, and the hydrofluoric acid liberated during the reaction causes corroding of the apparatus. Furthermore, the production of the starting products required is expensive.

In the case of these processes known hitherto, hydrolysis to give squaric acid has to be performed at a temperature of at least 100° C. and, for the purpose of improving the yield, in a strongly acid medium, generally in at least 50% sulphuric acid, or with the addition of concentrated hydrochloric acid, a procedure which, on account of the waste liquors occurring is undesirable also from an ecological point of view. If hydrolysis is performed in a weakly acid medium or in water, the yields are unsatisfactory, even with prolonged reaction times.

It is also known that 4,5-dichloro-1,3-dioxol-2-one (dichlorovinylene carbonate) can be dimerised on irradiation in acetone to two stereoisomeric cyclobutane derivatives, which by hydrolysis are converted to octahydroxycyclobutane. The octahydroxycyclobutane can be transformed by reaction with $SO_2$ into squaric acid [see 'Angew. Chemie' (Applied Chemistry), 86, 567 (1974)]. The 4,5-dichloro-1,3-dioxol-2-one used as starting product has to be produced from 1,3-dioxol-2-one by a costly synthesis comprising several stages.

Finally, squaric acid can be obtained, according to the German Offenlegungsschrift No. 2,235,882 and Gazzetta Chim. It., 102, 818 (1972), also by electrolytic reductive cyclotetramerisation of CO in non-aqueous solution at elevated pressure, preferably at a pressure of between about 90 and 350 atm. Complicated apparatus of a special kind is required for this process.

It was therefore the object of the invention to render accessible squaric acid in a simple and economic manner and with avoidance of the aforementioned disadvantages.

It has been found that it is possible to produce with the use of readily obtainable starting products, in an economical manner and with good to very good yields, new intermediates which can be easily converted under mild reaction conditions into squaric acid.

The new intermediates correspond to the formula I

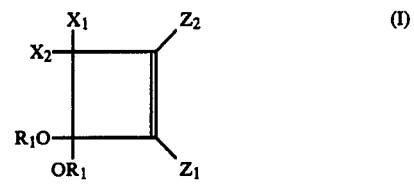

wherein $X_1$ and $X_2$ represent a group —$OR_1$, $Z_1$ represents a halogen atom or a group —$OR_2$, and $Z_2$ represents a group —$OCOCH_2$-halogen or —$OCOCH_2OR_2$; or $X_1$ and $X_2$ together represent the grouping =O, $Z_1$ represents a group —$OR_1$, and $Z_2$ represents a halogen atom or a group —$OR_2$; with $R_1$ representing a primary or secondary alkyl group having 1–4 carbon atoms, and $R_2$ an alkyl group having 1–4 carbon atoms or an alkanoyl group having 2–4 carbon atoms.

By the formula I are hence embraced cyclobutenes of the formula Ia

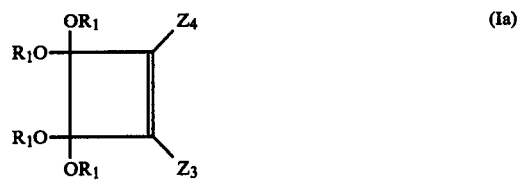

and cyclobutenones of the formula Ib

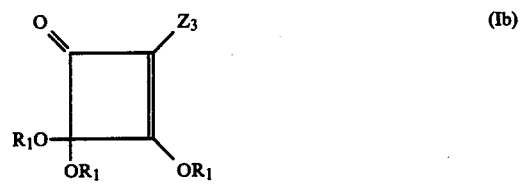

wherein $Z_3$ represents a halogen atom or a group —$OR_2$, $Z_4$ represents a group —$OCOCH_2$-halogen or —$OCOCH_2OR_2$, and $R_1$ and $R_2$ have the meanings given under the formula I.

The compounds of the formula I can be produced by a new process, which process comprises reacting a compound of the formula II

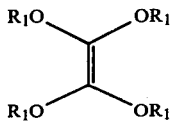 (II), in the presence of an organic base, with a halide of the formula III

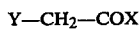 (III)

wherein
Y represents a halogen atom or a group —$OR_2$, and
X represents chlorine or bromine, and
$R_1$ and $R_2$ have the meanings given under the formula I.

Acting as the actual 2+2 cycloaddend is in this case a ketene of the formula

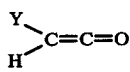

which is formed in situ by dehydrohalogenation with the organic base from the acid halide of the formula III. By the process according to the invention are surprisingly formed exclusively compounds of the formula I, although according to the literature [Chem. Berichte (Chemical Reports), 104, 873 (1971) and German Offenlegungsschrift No. 2,616,756] the cycloaddition of ketene or diphenylketene to tetraalkoxyethylene leads to oxetanes and/or cyclobutanones of the formulae IV and V

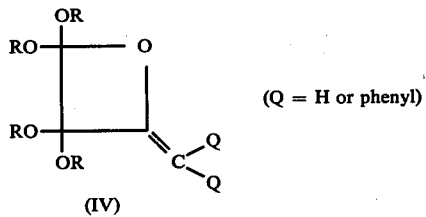 (Q = H or phenyl) 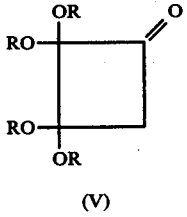

(IV)  (V)

The following may be mentioned as examples of alkyl groups $R_1$ as defined: the methyl, ethyl, n-propyl, isopropyl, or n-butyl, sec- and iso-butyl groups.

Alkyl groups $R_2$ can be primary, secondary or tertiary. Alkanoyl groups $R_2$ can be primary or secondary. Examples of alkyl groups $R_2$ are the groups mentioned above under $R_1$, and also the tert.-butyl group. Examples of alkanoyl groups $R_2$ are the acetyl, propionyl, butyryl or isobutyryl group.

$R_1$ and $R_2$ represent, preferably independently of one another, the methyl or ethyl group.

Halogen atoms represented by $Z_1$, $Z_2$, $Z_3$ or Y, or the halogen in groups —$OCOCH_2$-halogen ($Z_2$ or $Z_4$) are, for example, bromine or fluorine atoms, especially however chlorine atoms.

X represents preferably chlorine.

Particularly preferred compounds of the formula I are those wherein $X_1$ and $X_2$ each represent a methoxy or ethoxy group, $Z_1$ represents a chlorine atom, a methoxy, ethoxy or acetyloxy group, $Z_2$ represents a group —$OCOCH_2Cl$, —$OCOCH_2OCH_3$, —$OCOCH_2OC_2H_5$ or —$OCOCH_2OCOCH_3$, and $R_1$ represents methyl or ethyl; or those wherein $X_1$ and $X_2$ together represent the grouping =O, $Z_1$ represents the methoxy or ethoxy group, $Z_2$ represents a chlorine atom, the methoxy or ethoxy group, and $R_1$ represents the methyl or ethyl group.

The tetraalkoxyethylenes of the formula II and the halides of the formula III are known, or can be produced by methods known per se. Tetraalkoxyethylenes can be obtained, for example, using the method described in Recueil, 92, 11 (1973), from dialkoxymonoaryloxymethanes.

The reaction of the tetraalkoxyethylenes of the formula II with the halides of the formula III is performed, as defined, in the presence of an organic base, and preferably in the presence of an inert organic solvent. Inert organic solvents which can be used are, for example: aromatic, aliphatic or cycloaliphatic hydrocarbons, such as benzene, toluene, xylenes, n-pentane, n-hexane, n-octane, cyclopentane or cyclohexane; aliphatic or cycloaliphatic ketones, such as acetone, methyl ethyl ketone, cyclopentanone and cyclohexanone; aliphatic and cyclic ethers, such as diethyl ether, tetrahydrofuran, tetrahydropyran and dioxane; and also nitriles of saturated aliphatic monocarboxylic acids having a total of 1–6 carbon atoms, such as acetonitrile, propionitrile, methoxypropionitrile and butyronitrile.

Aliphatic, cycloaliphatic and aromatic hydrocarbons, particularly alkanes having 5–8 carbon atoms, cyclopentane, cyclohexane, benzene and toluene are preferred.

The reaction can however be performed also without the addition of an inert organic solvent.

As organic bases in the process according to the invention there can be used, e.g., tertiary amines, especially trialkylamines each having 1–4, particularly 1 or 2, carbon atoms in the alkyl moieties, cyclic amines such as pyridine, quinoline, N-alkyl-pyrrolidines, N,N'-dialkyl-piperazines and N-alkylmorpholines, or dialkylanilines each having 1 or 2 carbon atoms in the alkyl moieties, e.g. N-methylpyrrolidine, N,N'-dimethylpiperazine, N-ethylmorpholine and dimethylaniline. Preferred bases are triethylamine and pyridine. The organic base can simultaneously serve also as solvent.

The reaction temperatures are in general between about 0° and 110° C. Reaction temperatures of between about 50° and 85° C. are preferred for the reaction with halides of the formula III wherein Y represents an alkoxy group as defined. The reaction with halides of the formula III wherein Y represents a halogen atom is however preferably performed at temperatures between about 0° and 20° C.

The tetraalkoxyethylene of the formula II and the halide of the formula III are used advantageously in a molar ratio of at least 1:2, i.e. in a stoichiometric amount. The halide however can be used in an amount which is less or more than the equivalent amount; and even where it is less, there are formed and isolated exclusively compounds of the formula I, and no oxetanes or cyclobutanones of the aforementioned formulae IV and V. The halide of the formula III is advantageously used however in an approximately 10–15% molar excess.

The organic base is advantageously used in a slight excess above the stoichiometrically required amount, preferably in an approximately 5–30% molar excess. If the organic base is simultaneously serving as solvent, it is employed advantageously in a 10–20-fold molar excess.

In the process according to the invention are formed, depending on the type of halide of the formula III, solely compounds of the formula Ia, or alternatively mixtures of compounds of the formulae Ia and Ib. If Y in the formula III represents an alkoxy or alkanoyloxy group as defined, there are in general formed exclusively compounds of the formula Ia, whereas mixtures of compounds of the formulae Ia and Ib are formed in the case where Y is halogen. By the addition of suitable catalysts, for example mixtures of silica gel and an organic base of the aforementioned kind, preferably triethylamine or pyridine, or neutral or basic aluminium oxide, the cyclobutenes of the formula Ia can be converted into the corresponding cyclobutenones of the formula Ib. The reaction is advantageously performed in an inert organic solvent. Suitable solvents are the classes of compounds given in the foregoing. The reaction temperatures are usually between about 0° and 30° C. A prior isolation of the cyclobutenes of the formula Ia is not absolutely necessary but generally advantageous.

The compounds according to the invention can be isolated and purified in a manner known per se, for example by filtration, concentration by evaporation, and distillation.

The present invention relates also to the use of the compounds of the formula I for producing squaric acid by hydrolysing a compound of the formula I, or mixtures thereof, in an acid medium. Suitable acids are in particular highly diluted HBr and HCl (about 5–20%); whilst for mixtures of compounds of the formulae Ia and Ib a suitable acid is under certain circumstances also concentrated sulphuric acid. The hydrolysis can optionally be performed in the presence of an organic solvent. Suitable for this purpose are in particular water-miscible organic solvents boiling below about 125° C., which serve as dissolving intermediaries, such as aliphatic or cyclic ethers or aliphatic alcohols having 1–6 carbon atoms, e.g. tetrahydrofuran and dioxane, ethylene glycol dialkyl ethers each having 1–4 carbon atoms in the alkyl moieties, such as ethylene glycol dimethyl ether and ethylene glycol diethyl ether, and also methanol, ethanol, butyl alcohol and hexyl alcohol. The hydrolysis even at temperatures below 100° C. and with the use of highly diluted HBr or HCl is generally finished within a few hours. The compounds of the formula I can be converted also without intermediate isolation directly into squaric acid. The reaction temperatures are preferably between about 20° and 80° C. The acid used is advantageously 18% hydrochloric acid.

Squaric acid is known and can be used, for example, as a sequestering agent (U.S. Pat. No. 3,059,030). It constitutes also a valuable intermediate for the production of pharmaceutical active substances, stabilisers for polyacetals or photographic emulsions, dyes, agricultural active substances, polyamides, etc. [see, e.g., German Offenlegungsschriften Nos. 2,251,679 and 2,616,756, French Patent Specifications Nos. 1,531,943 and 2,046,068, Angew.Chem., 77, 680 (1965), Internat. Symp.Macromol. Chem. Prep. 1, 31 (1969) and Polymer, 14 (5), 230-1 (1973)].

EXAMPLE 1

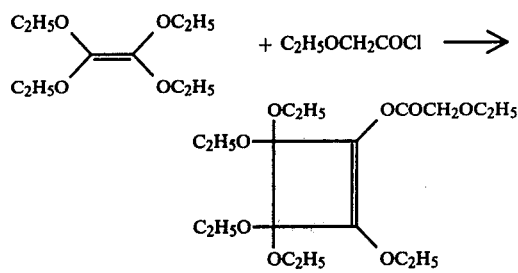

27 g (0.22 mole) of ethoxyacetic acid chloride is added dropwise to a solution of 20.4 g (0.1 mole) of 1,1,2,2-tetraethoxyethylene and 23.1 g (0.23 mole) of triethylamine in 50 ml of absolute n-hexane, whilst vigorous stirring and refluxing of the solution is being maintained. The white suspension formed is refluxed for a further 7 hours, then cooled and filtered. The liquid filtrate concentrated by evaporation (34.3 g of a yellow oil; 91.2% of theory) is distilled at 120°–125° C./0.01 Torr to yield 30.8 g (82% of theory) of 2,3,3,4,4-pentaethoxy-1-ethoxyacetoxy-cyclobutene.

IR spectrum (liquid): 5.6; 5.79; 7.78 μ.

NMR spectrum (CDCl$_3$): 1.1–1.5 (m, 18H, 6xCH$_3$); 3.45–3.95 (m, 10H, 5x-OCH$_2$); 4.12 (q, 2H, —OCH$_2$— in position 2) and 4.18 ppm (s, 2H, —COCH$_2$O— in position 1).

Analysis for C$_{18}$H$_{32}$O$_8$ (molecular weight 376.45):

| | | | |
|---|---|---|---|
| calculated: | C 57.43% | H 8.57% | O 34.00% |
| found: | C 56.88% | H 8.52% | O 34.30% |

EXAMPLE 2

If there is used in Example 1 only 12.3 g (0.1 mole) of ethoxyacetic acid chloride, with otherwise the same procedure, there is obtained, according to combined gas-chromatographical and NMR analysis, 49% of non-reacted 1,1,2,2-tetraethoxyethylene and 44% of 2,3,3,4,4-pentaethoxy-1-ethoxyacetoxy-cyclobutene. The analysis of the distillates gives the same result.

EXAMPLE 3

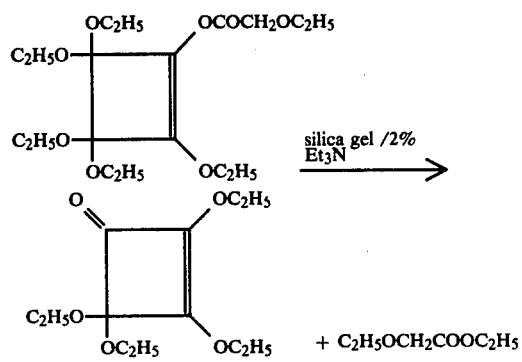

100 g of silica gel and 2 g of triethylamine are added to a solution of 7.52 g (20 millimoles) of 2,3,3,4,4-pentaethoxy-1-ethoxyacetoxy-cyclobutene, produced according to Example 1, in 100 ml of n-hexane, and stirring is then maintained for 2 hours at 20°–25° C. After filtering off the silica gel and concentrating the filtrate by evaporation, there is obtained, by chromatography on silica gel (eluant=mixture of hexane and diethyl ether in the volume ratio of 3:2), 4.15 g (85% of theory) of 2,3,4,4-tetraethoxycyclobutenone in the form of a colourless oil.

IR spectrum (liquid): 5.62; 6.09; 7.51 μ.

UV spectrum (ethanol): 251 (ε=12400), 296 (shoulder, ε=264)nm,

NMR spectrum (CDCl₃): 1.27+1.34+1.45 (3xt, 6H+3H+3H, 4x —CH₃); 3.8 (q, 4H, —OCH₂— in position 4) and 4.35+4.46 ppm (2xq, 2x 2H, —OCH₂— in positions 2 and 3).

Analysis for $C_{12}H_{20}O_5$ (molecular weight 244.29):

| | | | |
|---|---|---|---|
| Calculated: | C 59.00% | H 8.26% | O 32.75% |
| found: | C 58.64% | H 8.22% | O 32.70% |

EXAMPLE 4

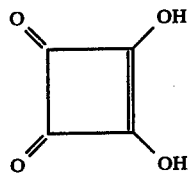

An emulsion of 18.7 g (0.05 mole) of 2,3,3,4,4-pentaethoxyethoxyacetoxy-cyclobutene, produced according to Example 1, in 190 ml of 18% hydrochloric acid is heated at 70° C. with very vigorous stirring. Already after 30 minutes, the first crystals of squaric acid are being precipitated. Heating is removed after one hour, and the reaction mixture is cooled with an ice bath to 0° C. After 2 hours, 3.5 g of reaction product (squaric acid) are filtered off, and washed with ice-cold water. The filtrate is concentrated by evaporation; the brown, oily-crystalline residue is stirred with 10 ml of a 1:1 volume mixture of benzene and acetonitrile, and the crystals of the squaric acid (1.45 g) are filtered off and washed with benzene. The total yield of squaric acid is 4.95 (87% of theory).

Decomposition temperature and decomposition temperature of a mixture with commercial squaric acid: 290°–295° C. (without melting).

IR spectrum (KBr): absorption bands at 4.15μ (broad, OH-hydrogen bridges); 5.5 and 6.05μ (carbonyl) and 6.6μ (C═C conjugation).

This IR spectrum is congruent with that of squaric acid obtainable commercially.

EXAMPLE 5

2.45 g (10 millimoles) of 2,3,4,4-tetraethoxycyclobutenone, produced according to Example 3, 35 ml of 12% HBr and 30 ml of dioxane are vigorously stirred at 40° C. After 8 hours' reaction time, volatile constituents are removed in vacuo (65° C./10 Torr). The crystalline residue is triturated with toluene, filtered and dried. There is thus obtained 1.0 g (88% of theory) of squaric acid. The IR spectrum of the substance obtained corresponds to that of commercial squaric acid.

EXAMPLE 6

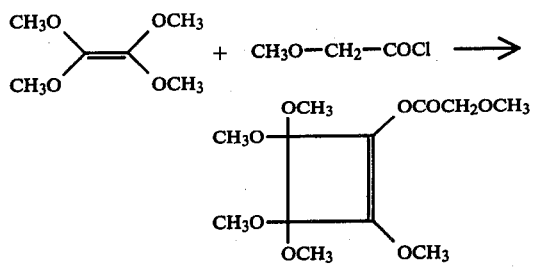

21.7 g (0.2 mole) of methoxyacetic acid chloride is added dropwise, with vigorous stirring, to a solution, heated to 70° C., of 14.8 g (0.1 mole) of 1,1,2,2-tetramethoxyethylene and 16.6 g (0.21 mole) of pyridine in 80 ml of absolute benzene. The suspension obtained is stirred at 70° C. for a further 5 hours, and subsequently cooled to 20° C. The pyridinium hydrochloride which has precipitated is filtered off, and the filtrate is concentrated at 11 Torr. There is obtain a cognac-coloured residue which contains, according to NMR analysis, 93±2% of 2,3,3,4,4-pentamethoxy-1-methoxyacetoxycyclobutene. For the purpose of obtaining the pure substance, a quarter of the residue is distilled at 110° C./0.015 Torr in a bulb tube to give 3.35 g (68% of theory, relative to ¼ of the employed 1,1,2,2-tetramethoxyethylene) of 2,3,3,4,4-pentamethoxy-1-methoxyacetoxy-cyclobutene.

IR spectrum (liquid): 5,6; 5.78; 6.9; 7.55; 7.72; 8.34; 9.1; 10.17μ.

NMR spectrum (CDCl₃): 3.44+3.49+3.52 (3xs, 6H+3H+6H, 5x —OCH₃); 3.84 (s, 3H, —OCH₃ in position 2) and 4.18 ppm (s, 2H, —COCH₂O— in position 1).

Analysis for $C_{12}H_{20}O_8$ (molecular weight 292.28):

| | | | |
|---|---|---|---|
| calculated: | C 49.31% | H 6.90% | O 43.79% |
| found: | C 49.00% | H 6.94% | O 43.99% |

EXAMPLE 7

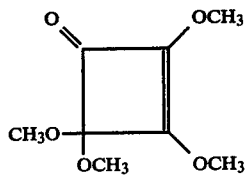

A quarter of the residue obtained according to Example 6 is dissolved in 20 ml of diethyl ether. This solution is added dropwise to a suspension, cooled to 0° C., of 40 g of aluminium oxide ("Woelm neutral" for column chromatography, activity 1) in 75 ml of diethyl ether. The ice bath is subsequently removed and the reaction mixture is stirred at 20°–25° C. for a further hour. The aluminium oxide is then filtered off, and washed well with diethyl ether. After removing by distillation the solvent and the formed methyl-methoxyacetic acid ester at 10 Torr, the resulting colourless residue is distilled in a bulb tube at 55°–60° C./0.1 Torr to obtain 1.78 g (54.5% of theory, relative to ¼ of the 1,1,2,2-tetramethoxyethylene used in Example 6) of 2,3,4,4-tetramethoxycyclobutenone as colourless oil.

IR spectrum (liquid): 5.6; 6.08; 6.8; 7.41; 9.32; 9.65; 11.62μ.

UV spectrum (methanol): 249 (ε=11100), 293 (shoulder, ε=210).

NMR spectrum (CDCl₃): 3.51 (s, 6H, 2x —CH₃ in position 4) and 4.0+4.11 ppm (2xs, 2x —CH₃ in position 2 and 3).

Analysis for $C_8H_{12}O_5$ (molecular weight 188.18):

| calculated: | C 51.06% | H 6.43% | O 42.51% |
|---|---|---|---|
| found: | C 50.77% | H 6.54% | O 42.87% . |

EXAMPLE 8

Half of the crude product obtained according to Example 6 is emulsified in 100 ml of 18% HCl and vigorously stirred. The emulsion is then immersed, with vigorous stirring, in a bath at 100° C. The first cyrstals of squaric acid are forming already after 3 minutes. The reaction mixture is cooled to 0° C. after 15 minutes, and after 30 minutes, the squaric acid which has formed is filtered off, and dried in vacuo at 10 Torr and 40° C. There is obtained 3.85 g (67.5% of theory, relative to half of the 1,1,2,2-tetramethoxyethylene used in Example 6) of squaric acid. A further 0.2 g of squaric acid is obtained by processing of the filtrate as described in Example 4. The total yield of squaric acid is 4.05% (71% of theory). The IR spectrum of the substance obtained corresponds to that of commercial squaric acid.

EXAMPLE 9

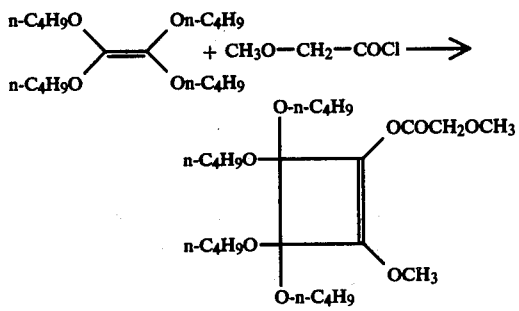

A solution of 11.4 g (0.105 mole) of methoxyacetic acid chloride in cyclohexane is added dropwise to a refluxing solution of 15.8 g (0.05 mole) of 1,1,2,2-tetra-n-butoxyethylene and 11.1 g (0.11 mole) of triethylamine in 40 ml of cyclohexane. The reaction mixture is refluxed for a further 6 hours, then cooled and filtered. The yellow filtrate, concentrated in vacuo (80° C./0.5 Torr), consists, according to NMR-analysis, to the extent of more than 95% of pure 2-methoxy-3,3,4,4-tetra-n-butoxy-1-methoxyacetoxycyclobutene. The yield is 19.8 g (86% of theory).

NMR spectrum (CHCl₃): 0.98 (bt, 12H, 4x CH₃); 1.1–1.9 (m, 16H, 8x CH₂); 3.4–3.9 (m, 8H, 4x —OCH₂—); 3.46 (s, 3H, —CH₂OCH₃ in position 1); 3.83 (s, 2H, —COCH₂O— in position 1) and 4.16 ppm (s, 3H, —OCH₃ in position 2).

Analysis for $C_{24}H_{44}O_8$ (molecular weight 460.61):

| calculated: | C 62.58% | H 9.63% | O 27.79% |
|---|---|---|---|
| found: | C 63.30% | H 10.09% | O 26.91% . |

EXAMPLE 10

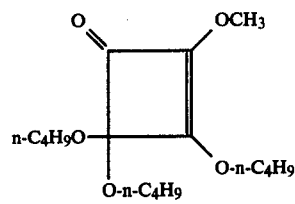

The procedure as described in Example 9 is followed. Before the formed triethylammonium chloride is filtered off however, there is added in small portions, to the well-stirred reaction suspension, 150 g of silica gel (Type 60, Firma Merck, for column-chromatography). The reaction mixture is then stirred for 3 hours at 20°–25° C., filtered, and concentrated in vacuo at 10 Torr. There is obtained from the liquid reaction residue, by vacuum distillation at 105°–110° C./0.005 Torr, 11.3 g (72% of theory) of 2-methoxy-3,4,4-tri-n-butoxycyclobutenone in the form of a colourless viscous liquid.

IR spectrum (liquid): 5.7; 6.08; 6.85; 7.96; 8.96; 9.3μ.

NMR spectrum (CDCl₃); 0.98 (bt, 3x CH₃); 1.2–1.9 (m, 8H, 4x CH₂); 3.6 (t, 4H, 2x —OCH₂— in position 4); 4.0 (s, —OCH₃ in position 2) and 4.38 ppm (t, 2H, —OCH₂— in position 3).

Analysis for $C_{17}H_{30}O_5$ (molecular weight 314.4):

| calculated: | C 64.94% | H 9.62% | O 25.44% |
|---|---|---|---|
| found: | C 64.62% | H 10.04% | O 24.67% . |

EXAMPLE 11

9.2 g (20 millimoles) of 2-methoxy-3,3,4,4-tetra-n-butoxy-1-methoxyacetoxycyclobutene, produced according to Example 9, and 60 ml of 5% HCl are vigorously stirred at 20°–25° C. for 24 hours. All volatile constituents are afterwards distilled off at 70° C./10 Torr, and the oily-crystalline residue remaining behind is stirred together with a 1:1 volume mixture of 15 ml of benzene and acetonitrile. There is obtained, on subsequent filtration of the reaction mixture, 1.53 g (67% of theory) of squaric acid. The IR spectrum of the substance obtained corresponds to that of commercial squaric acid.

EXAMPLE 12

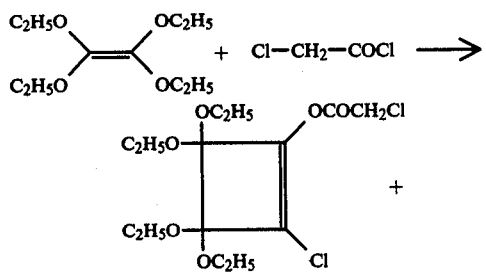

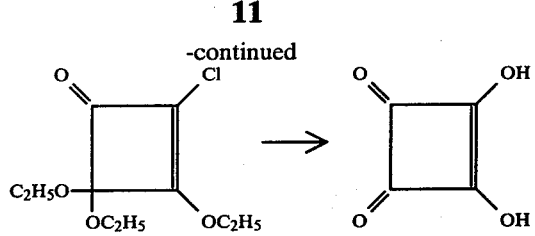

A solution of 46.4 g (0.41 mole) of freshly distilled chloroacetic acid chloride in 80 ml of absolute diethyl ether is added dropwise, with vigorous stirring, to a solution, held at 0° C., of 40.8 g (0.2 mole) of 1,1,2,2-tetraethoxyethylene and 44.3 g (0.44 mole) of triethylamine in 120 ml of absolute diethyl ether. The reaction mixture is subsequently stirred for 2 hours at 0° C. and then for 2 hours at 20° C. After filtration of the reaction mixture, the volatile constituents of the filtrate are removed by distillation at 50° C./10 Torr. The intensive IR-absorption bands of the liquid brown residue (62 g) confirm the formation of 2-chloro-3,3,4,4-tetraethoxy-1-chloroacetoxycyclobutene (5.71μ) and 2-chloro-3,4,4-triethoxycyclobutenone (5.59; 6.11μ). This crude-product mixture cannot be further separated on account of its thermal and hydrolytic instability.

31 g of this mixture and 60 ml of concentrated $H_2SO_4$ are heated, with vigorous stirring, for 90 minutes at 100° C. The reaction mixture is afterwards cooled to 0° C., and filtered after 16 hours. The dark crystals which have precipitated are washed with cyclohexane, and then dissolved in 90 ml of boiling water. The solution obtained is decolorised by the addition of active charcoal and filtered. The filtrate is concentrated by evaporation to 30 ml and cooled to 0° C. After 5 hours, the white crystals which have precipitated are filtered off. There is thus obtained 6.6 g (58% of theory, relative to half of the 1,1,2,2-tetraethoxyethylene used in the above Example) of squaric acid. The IR spectrum of the substance obtained corresponds to that of commercial squaric acid.

EXAMPLE 13

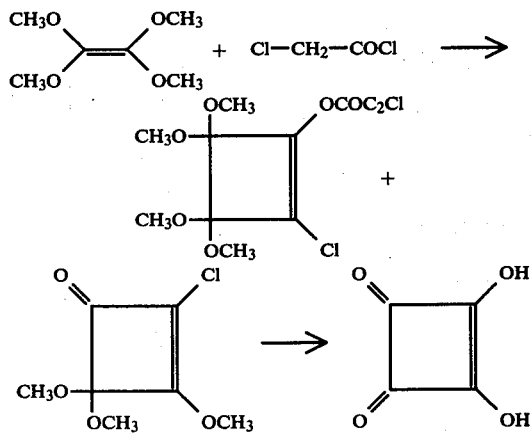

A solution of 23.7 g (0.21 mole) of chloroacetyl chloride is added dropwise, in the course of 40 minutes, to a solution, cooled to 0°–5° C. and vigorously stirred, of 14.8 g (0.1 mole) of 1,1,2,2-tetramethoxyethylene and 23.2 g (0.23 mole) of triethylamine in 100 ml of absolute n-hexane. The greyish-brown suspension formed is stirred for 3 hours at 20° C.; the resulting salt is then filtered off with suction and washed with n-hexane, and the yellow filtrate is concentrated by evaporation. The intensive IR-absorption bands of the residue (30.4 g) confirm the formation of 2-chloro-3,3,4,4-tetramethoxy-1-chloroacetoxycyclobutene (5.71μ) and 2-chloro-3,4,4-trimethoxycyclobutenone (5.58; 6.1μ). According to the NMR spectrum, the reaction mixture contains 80±5% by weight of 2-chloro-3,3,4,4,-tetramethoxy-1-chloroacetoxybutene and 12±3% by weight of 2-chloro-3,4,4-trimethoxycyclobutenone, besides small amounts of unidentifiable by-products. By rapid separation by columnchromatography of 0.5 g of the crude residue, it is possible to obtain 0.1 g of pure 2-chloro-3,4,4-trimethoxycyclobutenone (eluant: hexane/diethyl ether in a volume ratio of 4:1).

IR spectrum (liquid): 5.58; 6.1; 6.9; 7.5; 8.9; 9.2; 12.48; 12.6μ.

NMR spectrum ($CDCl_3$): 3.52 (s, 6H, 2x —$OCH_3$ in position 4) and 4.27 ppm (s, —$OCH_3$ in position 3).

A further separation of the crude-product mixture is not possible on account of its thermal and hydrolytic instability, but the mixture can be converted, as described in the preceding Example 12, directly into squaric acid.

EXAMPLE 14

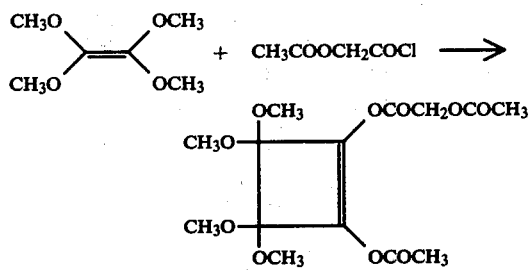

40.6 g (0.3 mole) of ethoxyacetic acid chloride is added dropwise, with vigorous stirring, to a refluxing solution of 20.4 g (0.138 mole) of 1,1,2,2-tetramethoxyethylene and 30.1 g (0.3 mole) of triethylamine in 100 ml of n-hexane. The reaction mixture is cooled after 3 hours and filtered. The oily crystals obtained are repeatedly washed with diethyl ether. The combined n-hexane and ether solutions are concentrated by evaporation. The residue (38.9 g of a brown oil; 81.5% of theory) contains, according to $^1$H-NMR spectrum, more than 95% of 1-acetoxy-acetoxy-2-acetoxy-3,3,4,4-tetramethoxycyclobutene.

IR spectrum (liquid): 5.6; 5.68; 5.80; 9.22μ.

NMR spectrum ($CDCl_3$): 2.18+2.21 (2xs, 6H, 2x —$COCH_3$); 3.50 (s, 12H, 4x $OCH_3$) and 4.73 ppm (s, 2H, —$COCH_2O$— in position 1).

EXAMPLE 15

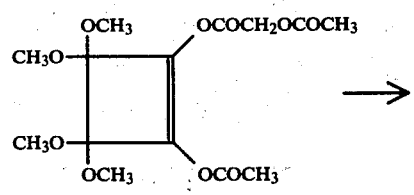

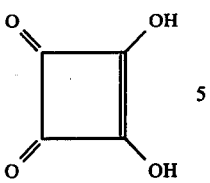

24 g of the crude cyclobutene obtained according to Example 14 is vigorously stirred in a mixture of 200 ml of 18% hydrochloric acid and 100 ml of dioxane for 30 minutes at 60° C. All volatile constituents are afterwards removed in vacuo (60° C./12 Torr); the residue is stirred with 50 ml of absolute acetone, and the greyish-white crystals are filtered of. There is thus obtained 5.5 g (74%) of squaric acid. The IR spectrum of the substance obtained corresponds to that of commercial squaric acid.

I claim:

1. A compound of the formula I

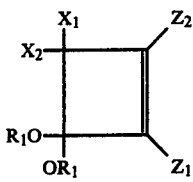

wherein
- $X_1$ and $X_2$ together represent the grouping =O,
- $Z_1$ represents a group —$OR_1$, and
- $Z_2$ represents a chlorine, bromine or fluorine atom or a group —$OR_2$; with
- $R_1$ representing a primary or secondary alkyl group having 1–4 carbon atoms, and
- $R_2$ an alkyl group having 1–4 carbon atoms or an alkanoyl group having 2–4 carbon atoms.

2. A compound of the formula I according to claim 1, wherein $X_1$ and $X_2$ together represent the grouping =O, $Z_1$ represents the methoxy or ethoxy group, $Z_2$ represents a chlorine atom, the methoxy or ethoxy group, and $R_1$ represents the methyl or ethyl group.

3. A compound according to claim 1, of the formula

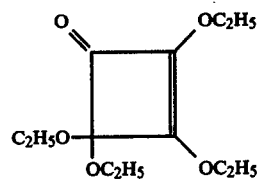

4. A compound according to claim 1, of the formula

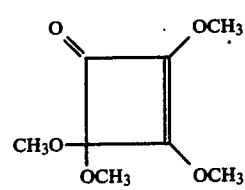

5. A compound according to claim 1, of the formula

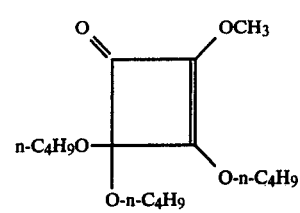

6. A compound according to claim 1, of the formula

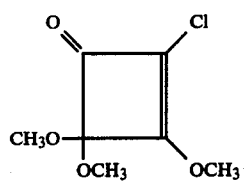

7. A compound of the formula I

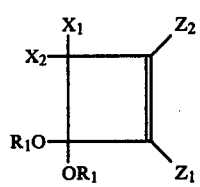

wherein
- $x_1$ and $x_2$ represent a group —$OR_1$,
- $Z_1$ represents a chlorine, bromine or fluorine atom or a group —$OR_2$,
- $Z_2$ represents a group —$OCOCH_2$—Cl, —$OCOCH_2$—Br, —$OCOCH_2$—F or —$OCOCH_2DR_2$,
- $R_1$ represents a primary or secondary alkyl group of 1 to 4 carbon atoms, and
- $R_2$ is an alkyl group of 1 to 4 carbon atoms or an alkanoyl group of 2 to 4 carbon atoms.

8. A compound of the formula I according to claim 7, wherein $X_1$ and $X_2$ are the same and each represent a methoxy or ethoxy group, $Z_1$ represents a chlorine atom, a methoxy, ethoxy or acetyloxy group, $Z_2$ represents a group —$OCOCH_2Cl$, —$OCOCH_2OCH_3$, —$OCOCH_2OC_2H_5$ or —$OCOCH_2OCOCH_3$, and $R_1$ represents methyl or ethyl.

9. A compound according to claim 7, of the formula

10. A compound according to claim 7, of the formula

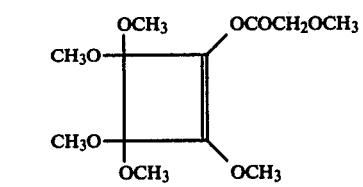

11. A compound according to claim 7, of the formula
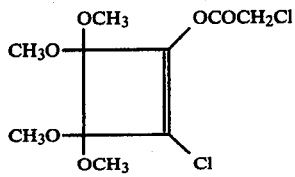
12. A compound according to claim 7, of the formula
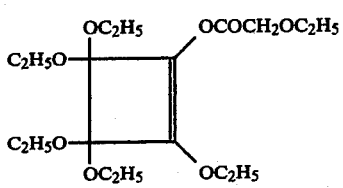
13. A compound according to claim 7, of the formula
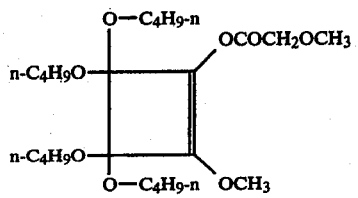
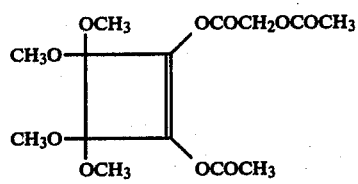
* * * * *